(12) United States Patent
Maceda

(10) Patent No.: US 10,072,240 B2
(45) Date of Patent: Sep. 11, 2018

(54) METHOD FOR MODULAR DESIGN, FABRICATION AND ASSEMBLY OF INTEGRATED BIOCOLUMN SYSTEMS WITH MULTIPLE DOWNSTREAM OUTPUTS

(71) Applicants: Singapore Technologies Dynamics Pte Ltd, Singapore (SG); Gibbs Energy, LLC, Plano, TX (US)

(72) Inventor: Joseph P Maceda, New York, NY (US)

(73) Assignees: SINGAPORE TECHNOLOGIES DYNAMICS PTE LTD, Singapore (SG); GIBBS ENERGY, LLC, Plano, TX (US)

(*) Notice: Subject to any disclaimer, the term of this patent is extended or adjusted under 35 U.S.C. 154(b) by 147 days.

(21) Appl. No.: 14/764,529

(22) PCT Filed: Dec. 31, 2013

(86) PCT No.: PCT/SG2013/000563
§ 371 (c)(1),
(2) Date: Jul. 29, 2015

(87) PCT Pub. No.: WO2014/120087
PCT Pub. Date: Aug. 7, 2014

(65) Prior Publication Data
US 2015/0376561 A1 Dec. 31, 2015

Related U.S. Application Data

(60) Provisional application No. 61/757,784, filed on Jan. 29, 2013.

(51) Int. Cl.
*C12M 1/00* (2006.01)
*C12M 3/00* (2006.01)
(Continued)

(52) U.S. Cl.
CPC ............. *C12M 21/12* (2013.01); *C10L 1/04* (2013.01); *C10L 3/08* (2013.01); *C12M 21/02* (2013.01);
(Continued)

(58) Field of Classification Search
CPC ...... C12M 21/02; C12M 23/58; C12M 23/06; C12M 23/44
See application file for complete search history.

(56) References Cited

U.S. PATENT DOCUMENTS 8,569,050 B1 * 10/2013 Ericsson .................. C12N 1/12
435/292.1
2003/0228684 A1 12/2003 Burbidge et al.
(Continued)

FOREIGN PATENT DOCUMENTS

DE 2037903 2/1971
WO 1981002898 10/1981
(Continued)

OTHER PUBLICATIONS

International Search Report for PCT/SG2013/000563, dated Feb. 11, 2014.

*Primary Examiner* — Nathan A Bowers
(74) *Attorney, Agent, or Firm* — Procopio, Cory, Hargreaves & Savitch LLP

(57) ABSTRACT

Present invention relates to a modular system for fabrication of a biocolumn for generating fuel stocks. The biocolumn of independent units called modules and which function as independent units and can be assembled together to fabricate a biocolumn. These modules can be assembled together to form various zones of biocolumn. Fuel stocks can be prepared by inputting a nutrient, a renewable energy source, photon energy and a carbon source into said zones and outputting fuel stock and by products from zones. The zones
(Continued)

are interconnected so that byproducts from each zone can be recycled as input or transformed into product.

7 Claims, 10 Drawing Sheets

(51) Int. Cl.
    *C10L 1/04*     (2006.01)
    *C10L 3/08*     (2006.01)

(52) U.S. Cl.
    CPC ............ *C12M 23/44* (2013.01); *C12M 31/10* (2013.01); *C12M 43/02* (2013.01); *C10L 2200/0469* (2013.01); *C10L 2290/26* (2013.01); *Y02P 20/59* (2015.11)

(56) References Cited

U.S. PATENT DOCUMENTS

| | | |
|---|---|---|
| 2007/0037259 A1 | 2/2007 | Hennessey et al. |
| 2010/0028976 A1* | 2/2010 | Hu .......... C12M 21/02 435/257.1 |
| 2010/0190227 A1* | 7/2010 | Dauth .......... C12M 21/02 435/168 |
| 2010/0267125 A1* | 10/2010 | Erb .......... C12M 21/02 435/292.1 |
| 2011/0195493 A1* | 8/2011 | Stroiazzo-Mougin .......... C12M 21/02 435/292.1 |
| 2011/0200954 A1 | 8/2011 | Sassow |
| 2011/0278219 A1* | 11/2011 | Skill .......... C12M 21/02 210/601 |
| 2012/0252105 A1* | 10/2012 | Ahrens .......... C12M 21/02 435/257.3 |
| 2012/0282677 A1 | 11/2012 | Brod et al. |

FOREIGN PATENT DOCUMENTS

| | | |
|---|---|---|
| WO | 2008127629 | 10/2008 |
| WO | 2009063296 | 5/2009 |
| WO | 2013144703 | 10/2013 |

\* cited by examiner

METHOD FOR MODULAR DESIGN, FABRICATION AND ASSEMBLY OF INTEGRATED BIOCOLUMN SYSTEMS WITH MULTIPLE DOWNSTREAM OUTPUTS

CROSS REFERENCE TO RELATED APPLICATION

This application, filed under 35 U.S.C. 371, is the U.S. national phase of International Patent Application Number PCT/SG2013/000563 filed on 31 Dec. 2013 which claims priority to U.S. Provisional Patent Application No. 61/757,784 filed on 29 Jan. 2013, all of which said applications are herein incorporated by reference in their entirety.

FIELD OF INVENTION

The present invention relates to a modular system for fabrication of a biocolumn. The system comprises of modules and submodules, which function as independent units and can be assembled together to fabricate a biocolumn.

BACKGROUND OF INVENTION

Currently, the petrochemical industry primarily relies on finding existing deposits of stored hydrocarbons for subsequent refinement into fuels or chemical feedstocks for chemical synthesizing or processing. Next, the fossil carbon atoms contained in the fuel are combusted, or thermally processed, which releases a gaseous carbon dioxide into the atmosphere as an emission. There are natural processes that reclaim $CO_2$ from the atmosphere, such as photosynthesis, weathering of rock and capture by marine organisms. However, the rate that the natural processes remove $CO_2$ from the atmosphere cannot keep up with the current rate of industrial $CO_2$ emissions. It would be advantageous to develop methods and systems by which the carbon dioxide emissions directly, or those already in the atmosphere, are used as a feedstock input to produce biogases, bioliquids and biosolids.

The value of renewable energies, like geothermal, solar, hydroelectric and wind are limited by the high cost of storage and the transportation infrastructure necessary to move that energy to population centers. Thus, it would be advantageous to develop methods and systems that can maximize the value of these renewable energy sources and allow for energy exports by converting that energy directly into biogases, bioliquids and biosolids which will be processed into higher density, fungible fuels that can be cost effectively moved using existing transportation infrastructure.

Nature has either scattered or isolated natural occurring microorganism colonies and their growth is limited by the availability of carbon, nutrients and energy. For, example geothermal vents are an abundant source of energy and nutrients that promotes growth of some thermophilic prokaryotes (bacteria and archaea). These prokaryotes are specially adapted to grow in these environments. However, their growth could be enhanced if there were other colonies of microorganisms present with which to exchange reaction products, by-products and energy. It would be advantageous to develop methods and systems that can collect and integrate dispersed microorganism colonies and maximize their growth by providing a continuous supply of carbon, nutrients and energy while continuously removing the by-products produced in forms of biogases, bioliquids and biosolids.

Nature has provided many organisms that use photosynthesis for growth. The function of these organisms has been to capture atmospheric carbon. However, the atmosphere, plants and soil detritus represent only a few hundreths of one percent of the world's carbon inventory (2,000 of over 100 million gigatonnes). The vast majority is stored as carbonates (~99.9%), in the ocean, either in solution (~38,000 gigatonnes), or as methane hydrates (~50,000 gigatonnes). Recent discoveries, at deep-ocean thermal vents and in layers well below light penetration, have shown that older, non-phototropic, bacterial species are carrying out photosynthetic-like processes under a wide range of conditions. These organisms live in symbiotic balance from the seafloor to the surface. It is important to remember that the phototropes, which are dependent on sunlight as their primary energy source, are the most recently evolved organisms. A majority of living species evolved without photosynthesis. Their populations are dependent on temperature, pH, nutrient availability and currents. It would be advantageous the develop methods and systems that can maximize the use of photosynthesis to release carbon from carbon dioxide by helping the growth of microorganism colonies that produce biogases, bioliquids and biosolids. In naturally occurring consortia, only 20% of the total algal and bacterial biomass is of phototropic origin.

A biocolumn is a fabricated system capable of providing the environment described above which is made up of a number of tanks, pumps, heat exchangers and other components and subsystems sized for the optimal growth of the full range of species with appropriate interspecies material transfer, nutrient injection, waste disposal and product removal. Historically, industrial process systems similar to this have been approached as traditional civil engineering projects and have been uniquely engineered for each installation. This has resulted in high capital costs and poor economics for the resultant energy produced. Over 50 years ago HJ Lang demonstrated that the total cost of a chemical process plant was four to seven time the cost of the equipment purchased. Today these factors vary from 4.7 to 6.9 depending on the process, materials, location and size of the industrial scale plant.

US2007037259 discloses a process for fuel feedstock comprising, delivering a nutrient to a renewable source and reacting said source with microorganisms under controlled conditions in a reactor and removing recovered product.

US2003/0228684 discloses a cylindrical core structure and sunlight exposed on topmost layers.

WO2008127629 discloses a land based biomass production constrained by the limited amount of material than can be produced per acre because of nutrient, soil and weather conditions. Aquatic species can be grown at far higher densities per unit area with far more consistency. Most bioreactors have focused on the growth of phototropic species. This invention, which relates to the field of fuel feedstock production, discloses a system designed to reproduce the interdependent consortia found in nature where the majority of the biomass is anaerobic and non-phototropic. Through careful control of nutrient inflow, pH, temperature, product and waste removal, the system can be tuned to sustain an ongoing microorganism "bloom" condition across the full range of resident species. It also allows for the production of directly usable fuel oils and biofilms as well as gas streams that can be converted to commercially useful chemicals using available process technology.

The modular design and assembly of biocolumn system lowers capital cost of biocolumn and reduce the time necessary to design and install them on each site.

The biocolumn systems of instant invention is more related to interconnections between zones and species and try to maintain the natural flow of nutrients, communication, waste products etc., before the introduction of external inputs. An unappreciated fact that is ignored by most monocultural algae projects is that in naturally occurring consortia, there is a significant amount of interspecies communication and symbiotic consumption of deceased algae and other waste products. This communication and consumption both triggers and supports growth. Therefore, it is an aspect of the invention that each zone has an interconnection with the preceding and subsequent zones facilitates this interzonal transfer of material and information as well as provide additional inlets for externally supplied nutrients and outlets for product harvest and removal of toxic waste products, if any.

The present invention relates to a biocolumn system wherein the product gases can be recycled back into the input source. This enhances the efficacy of the system.

The present invention also provides a system for fabrication of a biocolumn, wherein the biocolumn is in form of modules. Modularization refers to the method of fabricating many of the components and subsystems. A key design parameter, is to make as much of the overall system factory-built and tested as possible.

There are several advantages associated with modularization of the biocolumn system. Uniquely designed plants are expensive because it is generally a single unit order and often involves custom engineering. Multiple unit orders and standardization of parts will quickly reduce the initial USD100, Purchased Equipment Cost significantly. Tanks, reactors, instrumentation, piping, electrical systems and buildings are individually bid and built on site. Integration of these subsystems into prefabricated modules reduces acquisition and installation costs. Further, the requirement of on-site labour is reduced by integrating service facilities into factory-built modules will reduce the requirement for on-site labor. Modularization reduces construction schedule and therefore the amount of on-site supervision. Furthermore, standardization reduces engineering from site-to-site to a simple analysis of the variation in feedstocks to determine handling, pre-treatment and mixing requirements. In brief, all of the above will reduce construction expenses; contingencies, working capital requirements and the total fixed capital investment.

In various zones of the biocolumn, carbon monoxide and other gases are produced. Some of these gases, such as methane, can be harvested immediately for such processes as Fischer-Tropsch Liquid (FTL) synthesis but there is never 100% conversion and carbon dioxide is directly produced by many of the bacterial and is also a by-product of the FTL systems. Although all algal biomass would be considered zero-net carbon, the limiting factor on carbon utilization is the total input quantity of carbon. Recycling effectively increases carbon input per unit of capital cost and enables an increase in overall carbon utilization, and therefore improving the system economics.

As to the benefits of modularization, it has been estimated that current cost projections for these types of systems shows reductions of as much as 50% in the capital cost of conventionally built system. As volumes grow, this is projected to climb as high as 70%.

In view of foregoing, it is evident that there arises a need to develop a system for fabricating biocolumn, which address the severe worldwide shortage of engineering, supervisory, installation, construction and operational personnel currently hampering the development of a wide range of industrial plants and facilities. These plants will be engineered and built in factories with the same level of skills as a shipyard or auto plant, two industries with massive overcapacity worldwide.

SUMMARY OF INVENTION

The objective of the current invention is to develop a method to reduce the cost and delivery time of biocolumn systems. A biocolumn system would be made up of a number of large vertical tanks made of steel or concrete, generally completely constructed on-site. The typical tank may have total solid content below 5% while some systems may reach levels as high as 25%. Vertical tanks may use some form of mixing but will always need methods of injecting nutrients, removing waste products while facilitating the interspecies communication that is necessary for consortial stability. There is a limit on the size of steel reactor tank that can be conveniently or affordably transported as a pre-assembled unit. As the size of installations has grown, built-in-place steel tanks on concrete footings have become the norm. These are expensive and time consuming to build.

The entire biocolumn system is designed in sections that are factory built. These sections are called modules, based on standard ISO shipping containers or other pre-fabricated structures and that can be mass-produced, shipped anywhere in the world, positioned on site, interconnected and commissioned.

According to an embodiment of the instant invention, all subsystems of the biocolumn can be modularized to the maximum extent possible including but not limited to insulation, heating, sensors, controls, interconnects, and safety. Necessary foundation footing forms and support buildings can also be prefabricated. Other than grading, compacting, trenching and concrete pouring no other fabrication or engineering will be needed on-site for fabricating and assembling the biocolumn system.

According to an aspect of the invention, there is provided a system for generating fuel stocks in a fabricated biocolumn comprising of various zones, fabricated by assembling modules of biocolumn, inputting nutrient(s), renewable energy source(s), photon energy and a carbon source into said zones and outputting fuel stock and by products from zones; wherein byproducts from each zone can be recycled back as input into any of the zone or transformed to a product for commercialization.

According to another aspect of the invention, there is provided a system for generating fuel stocks in a fabricated biocolumn, wherein each module can further be divided into submodules.

According to another aspect of the invention, there is provided a system for generating fuel stocks in a fabricated biocolumn, wherein submodules are assembled to fabricate a module.

According to another aspect of the invention, there is provided a system for generating fuel stocks in a fabricated biocolumn, wherein photon energy is obtained from submerged LED.

According to another aspect of the invention, there is provided a system for generating fuel stocks in a fabricated biocolumn, wherein said renewable energy source is a geothermal energy, a solar thermal energy, a photovoltaic energy, an external waste heat, a heat of internal reactions or combinations thereof.

According to another aspect of the invention, there is provided a system for generating fuel stocks in a fabricated biocolumn, wherein said nutrient is selected from the group consisting of a geothermal fluid, an organic waste slurry biomass, a coal, a hydrocarbon and combinations thereof.

According to another aspect of the invention, there is provided a system for generating fuel stocks in a fabricated biocolumn wherein said nutrient is water containing.

According to another aspect of the invention, there is provided a system for generating fuel stocks in a fabricated biocolumn, wherein said carbon source is selected from the group consisting of atmospheric air, a carbon dioxide source, an organic waste, a coal, a hydrocarbons, a geothermal fluid, an internal product of said consortium growth, propagation and reaction, and combinations thereof.

According to another aspect of the invention, there is provided a system for generating fuel stocks in a fabricated biocolumn wherein said modules are interconnected to function as a complete biocolumn.

DETAILED DESCRIPTION OF THE INVENTION

The present invention provides a modular structure of an open system, called biocolumn, which systematizes consortia under man-made conditions that maximizes the rate of conversion of carbon to biomass. Subsequently, this biomass can be used directly or converted to gases, chemicals, fuels or other commercial products. Using non-fungible available and renewable thermal energy sources to drive these processes will allow them to be converted to fungible products. This invention discloses a system for fabricating a biocolumn. The system of instant invention comprises of modules, which can be assembled onsite. The system lowers the capital cost and reduces site installation time of biocolumn systems.

The present invention involves use of a multi-level array of LEDs space to maximize the amount of algae exposed to the light in spite of the blocking effect of the algae in the water. Unlike conventional trough or tube photobioreactors, this type of array will allow for even light distribution throughout the entire volume of the tank.

In an embodiment of the invention, the array of LED includes LEDs arranged approximately six inches apart vertically.

According to an aspect of the invention, LEDs operating at a fraction of the normal intensity of sunlight (approximately one-sixth) at just the level at which algae growth plateaus, before additional light intensity is wasted or actually inhibits additional growth, are used.

According to another aspect of the invention, LEDs that are pulse to allow the proximate algae to recover from the acceptance of a photon and be ready to receive another are used.

According to another aspect of the invention, LED fixtures that are mounted on distributing tubes that provide nutrient input in such a manner as to sweep the LED lenses and prevent growth buildup that would block the light, are used.

Figure 1:
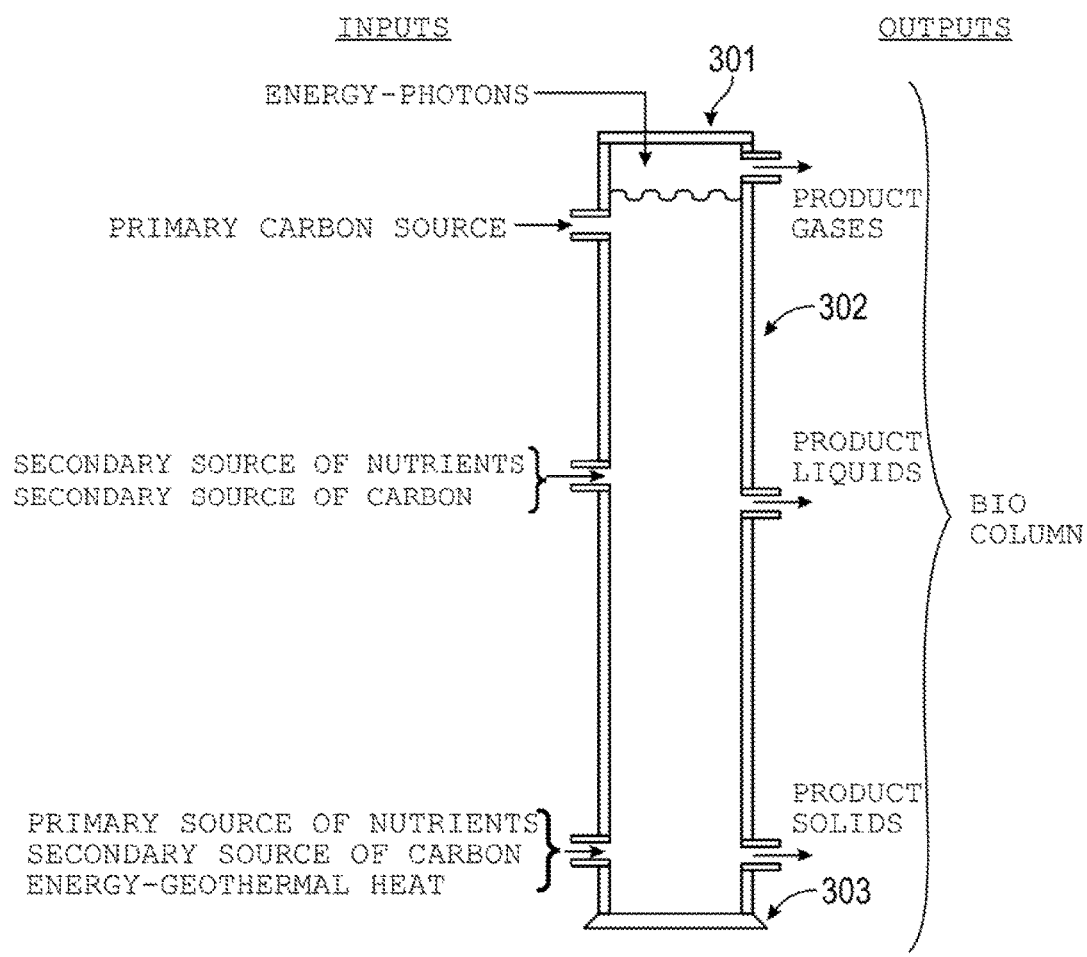
FIG. 1 is a conceptual diagram of a biocolumn known in prior art, with energy, carbon and nutrient inputs to a structure and showing outputs of product gases, liquids and solids.
Figure 2:
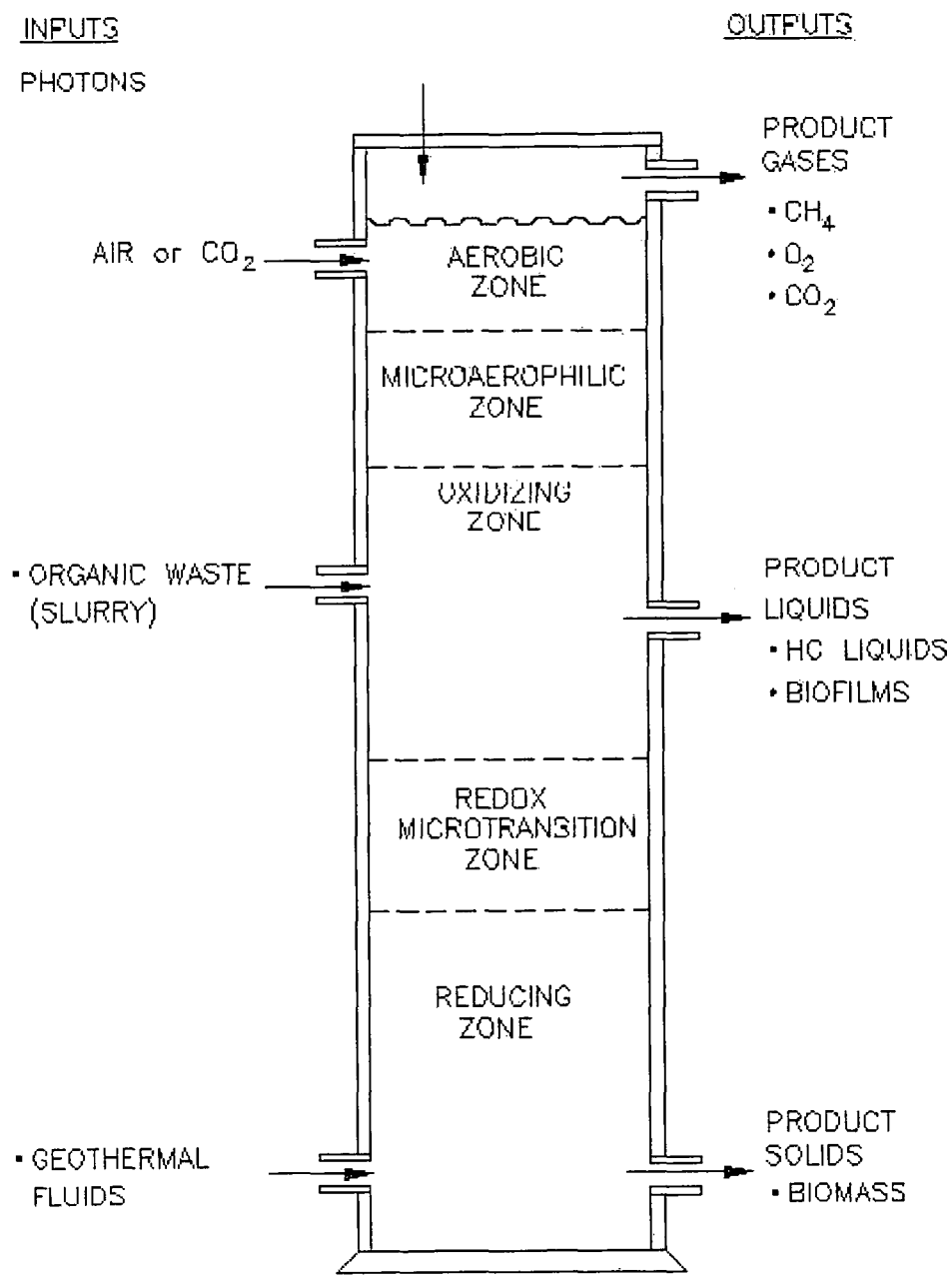
FIG. 2 is a conceptual diagram of a biocolumn known in prior art, indicating the possible sources of energy, carbon and nutrient inputs for the biocolumn at selected zones and the possible outputs of desired product gases, liquids and solids.

FIG. 1 and FIG. 2 describes biocolumn of prior art. The biocolumn system as shown in FIGS. 1 and 2 consist of several discrete zones that will need to be maintained at different temperatures and pH levels in order to maintain optimal nutrient feed rates, ii) harvest products, and, iii) remove waste necessary to support optimal growth rates of algal biomass. Biocolumn has a column cap 301 and a column wall 302 and a column base 303. These zones are:
1. Aerobic Zone,
2. Microaerophilic Zone,
3. Oxidizing Zone,
4. Redox Microtransition Zone, and
5. Reducing Zone.

Due to the different growth rates and lifespan of the various species, and their individual requirements for nutrients, each of these zones are housed in separate tanks sized to support the maximum overall biomass production rate for the integrated biocolumn system.

Figure 3:
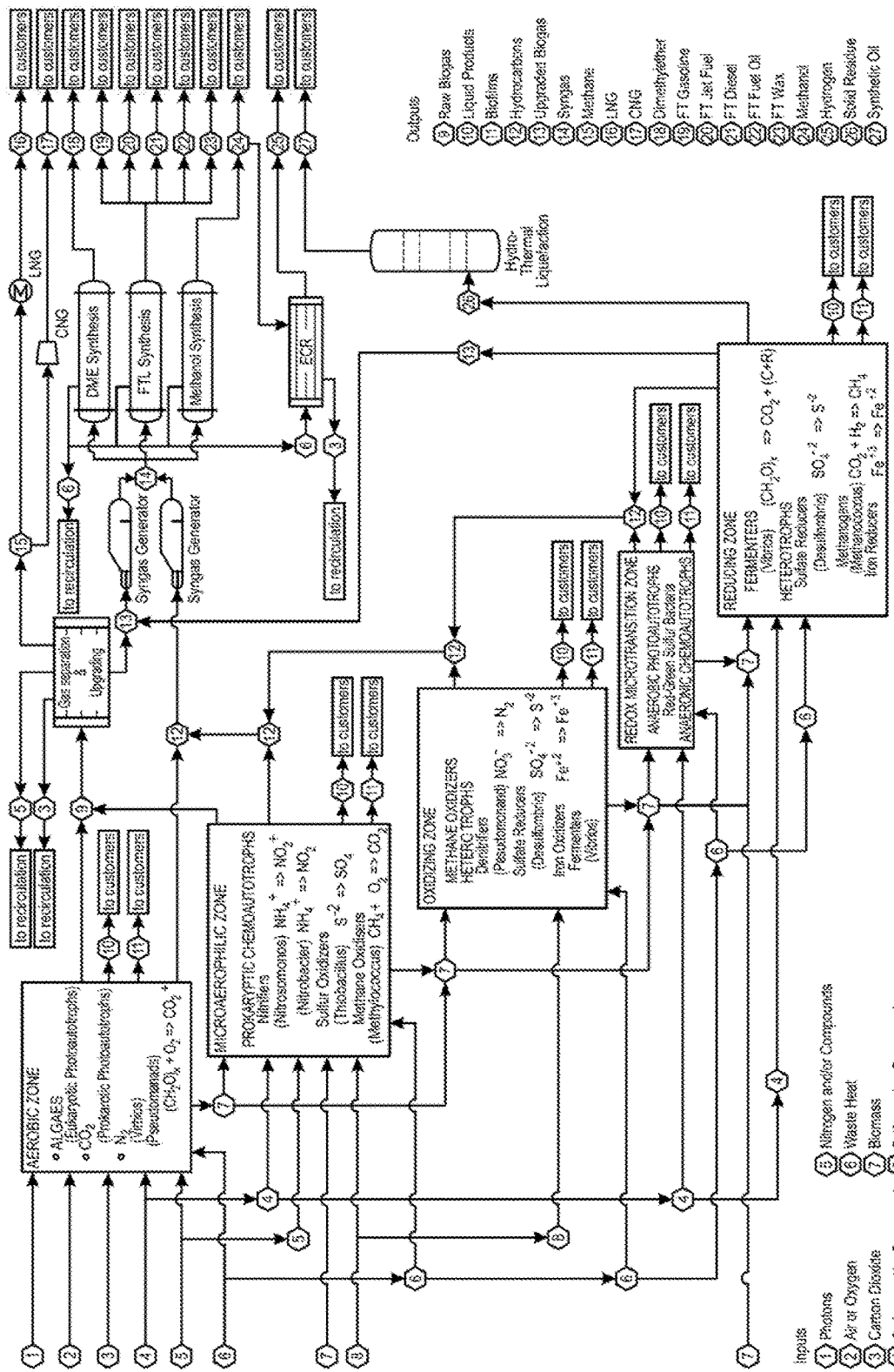
FIG. 3 depicts a conceptual process flow diagram of a biocolumn system with potential input and output sources indicated as well as downstream processing of commercial products.

FIG. 3 shows a conceptual process flow diagram for an integrated biocolumn system, including multiple downstream processing subsystems that will create salable products from all gaseous, liquid and solid output streams. Upstream input preprocessing options have been omitted to simplify this description. The Aerobic Zone is capable of receiving the widest range of substrate inputs, photons, air, oxygen, carbon dioxide, carbon, nitrogen and their compounds. In addition to the chemical potential of the substrates, photons and heat will also provide useful energy input.

In the Aerobic zone community the following will form:
1. Algaes
(Elikaryotic photoautotrophs)
2. cyanobacteria
(prokaryotic photoautotrophs)
3. Heterotrophs
(vibrios)
(pseudomonades) $(CH_2O)x + O_2 \rightarrow CO_2 +$ Depending on the range of available inputs and locally viable species, this zone may be further broken up into separate tanks to increase total biomass output or to focus on any readily harvestable outputs that can be directly sold as products or used as precursors in downstream manufacturing processes in such markets as cosmetics and pharmaceuticals.

Although energy output is the primary goal of the system, overall system profitability is the ultimate guide to output optimization. This is the same path that the oil industry has followed in the evolution of refining. Large quantities of commodity fuels are produced with the overall income stream being supplemented by the production of small amounts of high-value products, such as lubricants.

The goal of this, and all other sections, is to determine the optimal feed rates of nutrients and the matching disposal rates of waste and useful products that can maintain growth at "bloom" rates without a population crash. Zone sizes are determined by the need to match the various input and output streams as well as the inter-zonal communication needed to support overall consortial stability.

Microaerophilic zone community, is deprived of the direct injection of oxygen, the following is formed:
1. Prokaryptic chemoautotrophs
   a. Nitrifiers
   (nitrosomonos) $NH_4^+ \rightarrow NO_2^+$
   (nitrobacter) $NO_4^+ \rightarrow NO_2$
   b. Sulfur oxidizers
   (thiobacillus) $S_2^- \rightarrow SO_4^{2-}$
   c. Methane oxidizers
   (methylococcus) $CH_4 + O_2 \rightarrow CO_2$ Below this is the Oxidizing Zone, which propagates:
1. Methane oxidizers
2. Heterotrophs
   Denitrifiers
   (pseudomonads) $NO_2^- \rightarrow N_2$
   Sulfate reducers
   (desulfombrio) $SO_4^{2-} \rightarrow S_2^-$
3. Iron oxidizers
   $Fe_2^+ \rightarrow Fe_3^+$ This is followed by Redox Microtransition Zone, which forms:
1. anaerobic photoanitotrophs
   red-green sulfur bacteria
2. heterotrotrophs
   anaerobic chemoautotrophs Final section of the biomass synthesis section of the biocolumn is Reducing Zone which supports:
1. fermenters (vibrios)
   $(CH_2O)x \rightarrow CO_2 + (C+R)$
2. heterotrotrophs
   Sulfur reducers (desulfovibrio)
   $SO_4^{2-} \rightarrow S_2^-$
3. methogens (methonococcus)
   $CO_2 + H_2 \rightarrow C$
4. iron reducers
   $Fe_3^+ \rightarrow Fe_2^+$ In all cases, a zone may be subdivided into a series of separately controlled and fed tanks to match the various growth rates, life spans, product harvesting, nutrient feeding and waste disposal requirements needed to maintain maximum biomass output.

After harvesting directly salable products from each section, where possible, the balance of the system output will be gaseous, liquid and solid. The gaseous component is biogas, a combination of methane and carbon dioxide. It also may include trace amounts of hydrogen sulfide which is recirculated to become sulfates elsewhere in the system.

This components of biogas are either separated, being recirculated or sold, or are converted to syngas, which can be made into a wide range of commercial products such as Fischer-Tropsch Liquids (FTL), alcohols and hydrogen. Modular subsystems, sized to match the output of the biocolumn system, are used to provide some, or all, of the biocolumn process heat requirement.

The liquid portion of the output consists of the various directly harvested products, i.e., oily species, biofilms, polysaccharides and water. The majority of the water comes from the concentration of the indigestible solids that are subsequently hydrothermally liquefied into synthetic crude oil. In an embodiment of the invention gasifiers are used to promote gasification.

FIG. 3 shows interconnections and transport of products and inputs in various zones of biocolumn of present invention. Photons (1), air or oxygen (2), carbon dioxide (3), carbon and/or compounds (4), nitrogen and/or compounds (5), waste heat (6), biomass (7) and sulfur and or sulfur compounds (8) are inputs for various zones. Photons (1), air or oxygen (2) and carbon dioxide (3) are directly input into Aerobic Zone. Carbon and/or Carbon compounds (4) can be input into any of the Aerobic zone, Microaerophilic zone, Redox microtransition zone or Reducing zone. Nitrogen and/or compounds of nitrogen (5) can be input into Aerobic zone and Microaerophilic zone. Waste heat produced from various zones (6) can be input into Aerobic zone and Microaerophilic zone, oxidation zone, Microtransition Zone and Reducing zone. Biomass (7) is a by-product of aerobic zone, and can be input into microaerophilic zone. Biomass (7) can be directly introduced into microtransition zone or reducing zone. Sulfur and or sulfur compounds (8) can be input into Microaerophilic zone. Raw biogas (9) and upgraded biogas obtained from various zones can be further sent for gas separation zone. Liquid products (10) and Biofilms (11) obtained from each zone can be directly commercialized to customers. Hydrocarbons (12) produced from various zones can be transferred to syngas generator. Syngas (14) generated from syngas generator can be further sent for methanol (24) synthesis, FTL (19) to (23) synthesis or DME (18) synthesis. Methane (15) obtained from gas separation unit can be further converted into CNG (16) or LNG (17) before commercialization. Methanol can be directed to ECR for production of hydrogen (25). Solid residue (24) obtained from reducing zone can be sent for hydrothermal liquefaction to obtain synthetic oil (27) for commercialization.

It is to be noticed that waste heat (6) is also recirculated to make the biocolumn in a more efficient and environment friendly manner.

Figure 4:
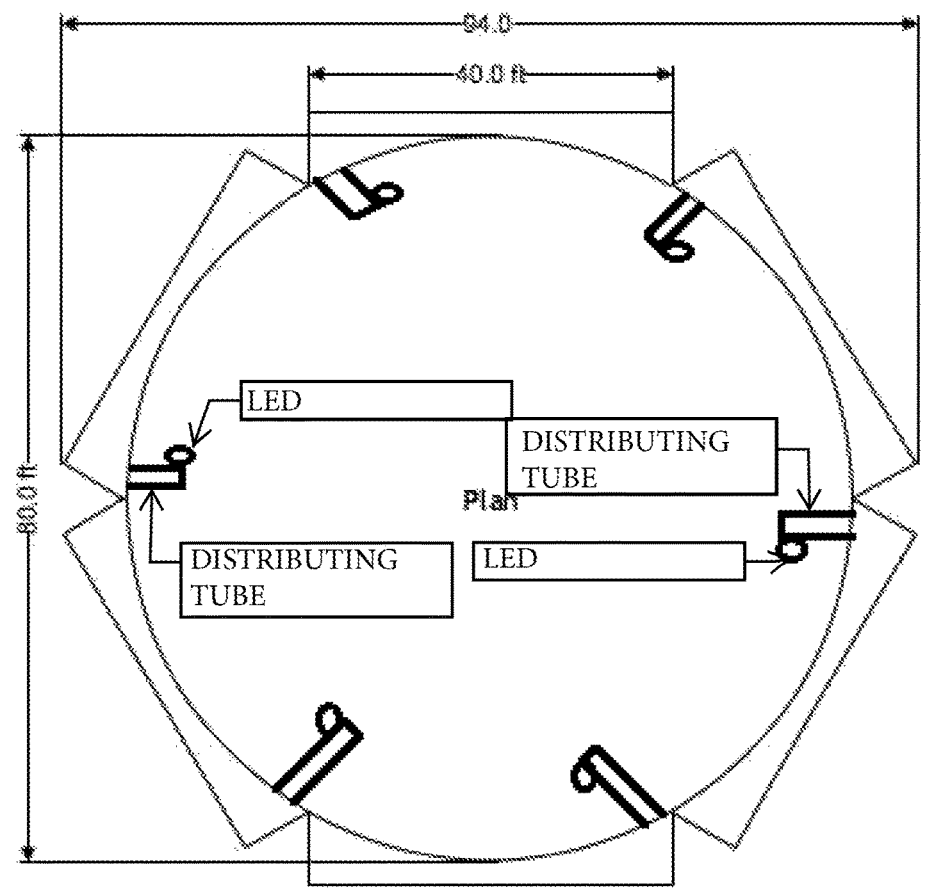
FIG. 4 depicts a plan view of a modular land-based biocolumn tank prefabricated in six 40 ft ISO shipping containers that are assembled on site into an 8'6" high ring, 80' in diameter.
Figure 5:
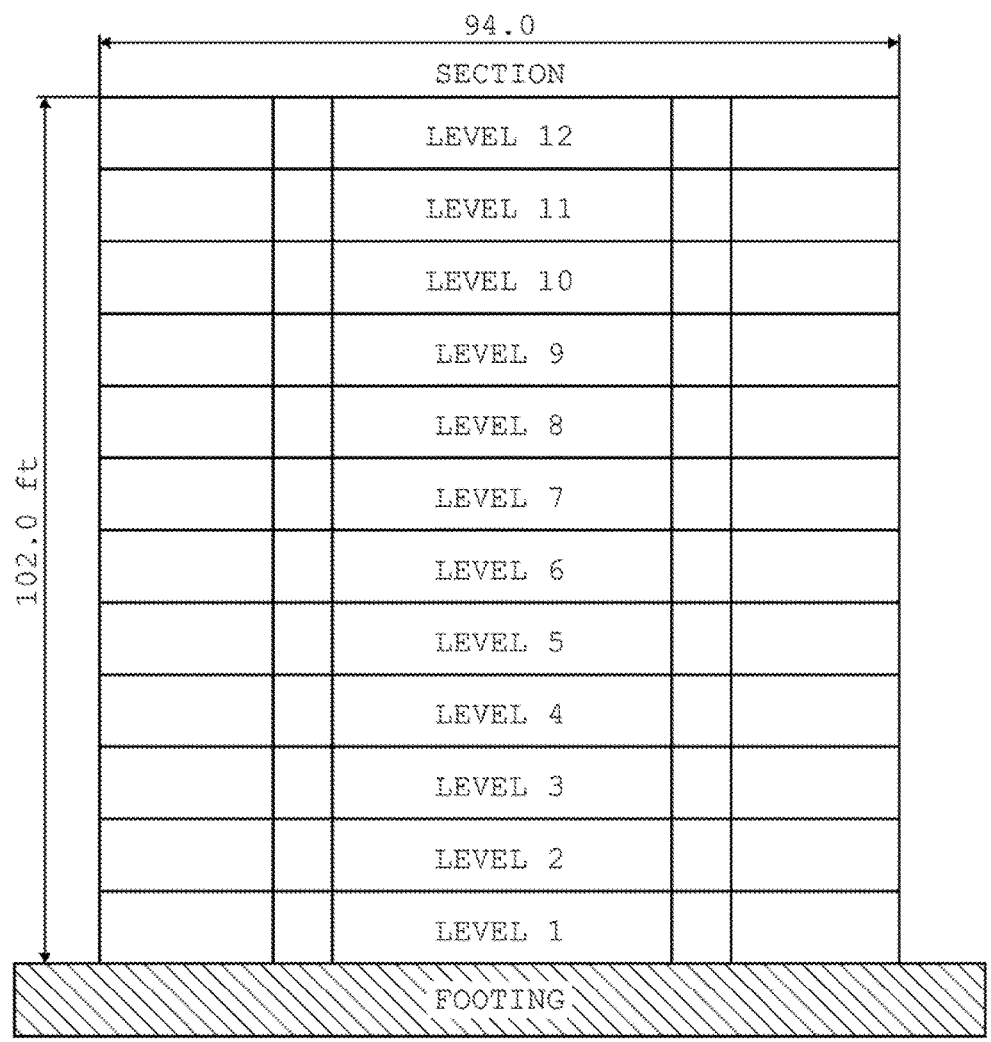
FIG. 5 depicts a side view of a modular, land-based biocolumn tank made up of twelve, six module rings assembled on site and supported on a concrete footing.

FIGS. 4 and 5 show a plan and cross section of a typical large tank (80' diameter) made up of six prefabricated sections per ring, stacked twelve units high. The rings are assembled on a footing poured over preassembled rebar cages delivered to the site. Each ring can climb up the side of the ring(s) below and slide into place. This means that the entire tank has 72 vertical welds 8'6" long and 144 horizontal welds of just under 49' long. With the precise registration provided by the ISO frames, simple robots are able to easily perform this function with precision and reliability. Each level represents an 8'6" high module based on the standard ISO shipping container specification. These modules fit together so the entire assembly creates a single tank that would be one zone of the biocolumn. This way each single module can replace about 12 to 18 individual bolt together pieces. This unit could be assembled in a day instead of weeks.

Figure 6:
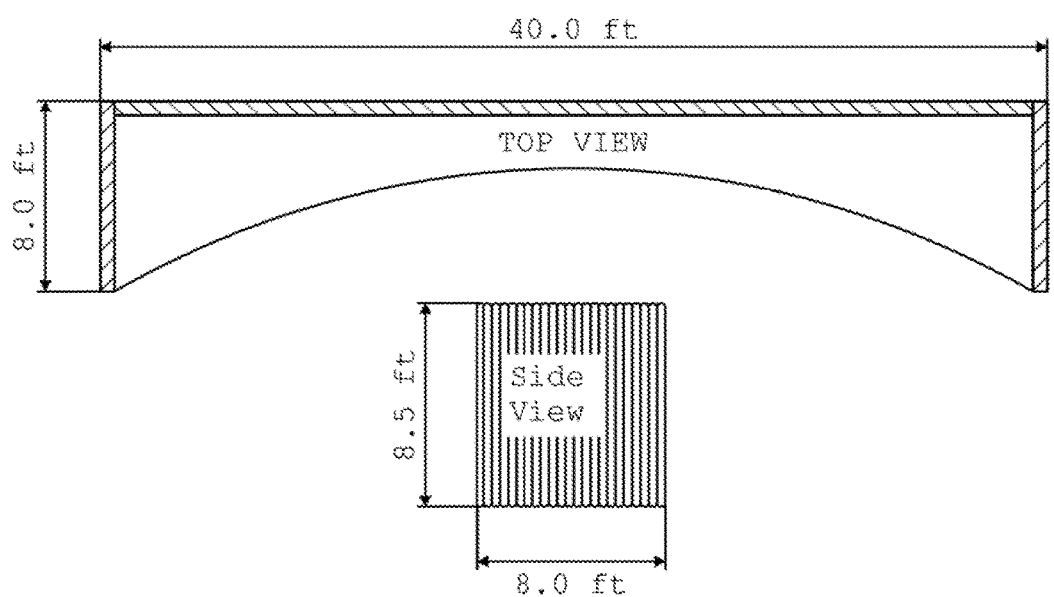
FIG. 6 depicts a single, 8'6" high, prefabricated tank wall module that makes up 60 degrees of a single ring of the biocolumn tank.

FIG. 6 shows a top and side view of a typical module used in the tank described above. This approach reduces part count, leak paths, assembly time, site labor and cost. The external form provides mounting for peripheral equipment and the entire assembly is covered in a fabric sleeve, with the dead air between the tank wall and sleeve providing sufficient insulation to maintain temperature in all weather conditions. The space between the curved inner wall and the straight outer walls is dead air space. Each inch has an insulating value of R=1. Pumps, wiring pipes etc. are mounted in these spaces with vertical access at the ends, which is covered with the overall fabric cover. This eliminates the need for onsite application of insulation and most of the labor for attaching all of the other external pieces. FIG. 6 shows a plan and section of one of the six units that would make up one level of FIG. 5. These can be factory built and shipped and handled with standard equipment.

Figure 7:
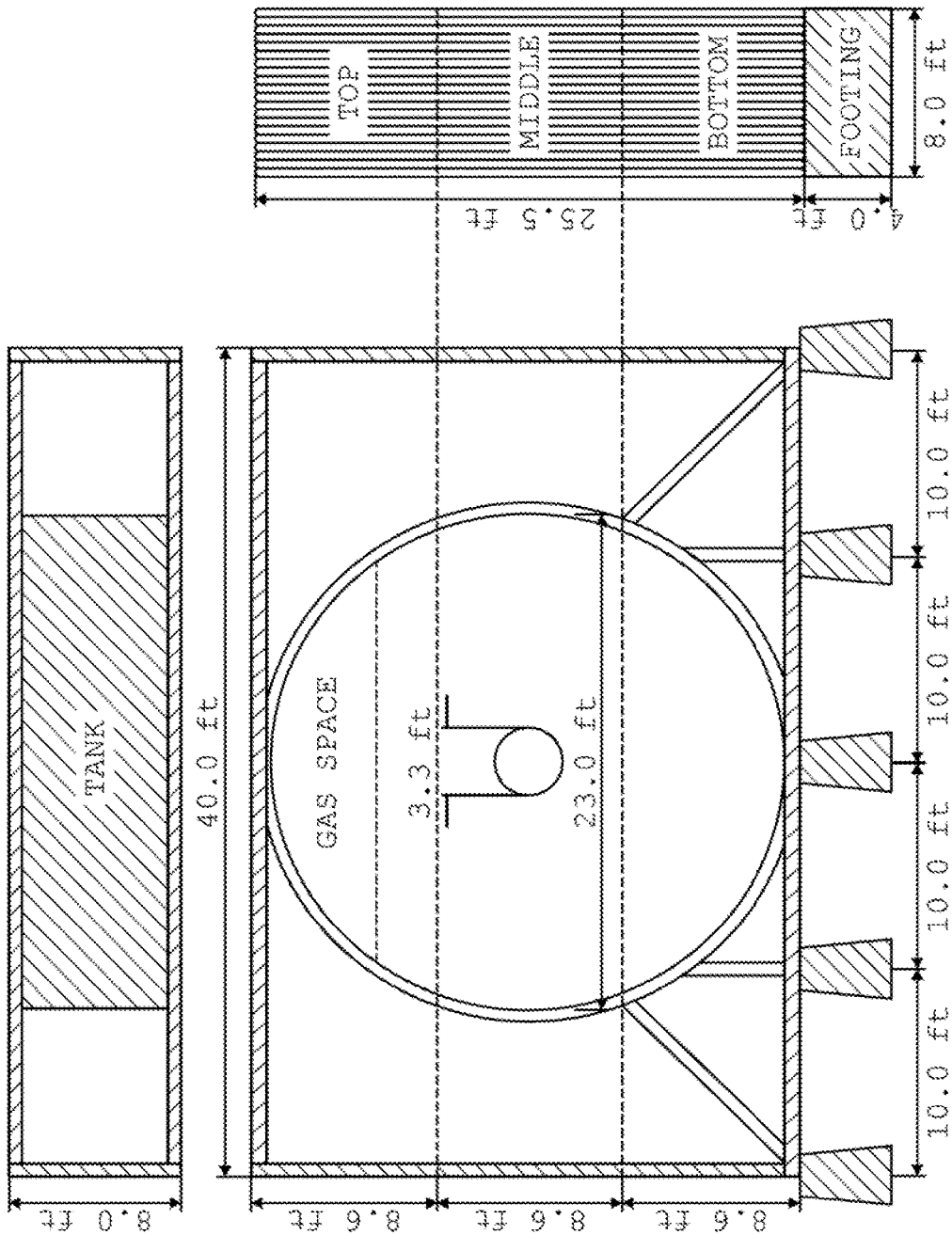
FIG. 7 depicts a plan view and two cross sections of a horizontal tank made up of three prefabricated modules.

FIG. 7 depicts a plan view and two cross sections of a horizontal tank made up of three prefabricated modules. When 15 of these assemblies are put together into a single plug-flow reactor, there is a screw feed at the input and output ends. An impeller can be used that slowly stirs and moves the material during its 15 day residence time.

Figure 8:
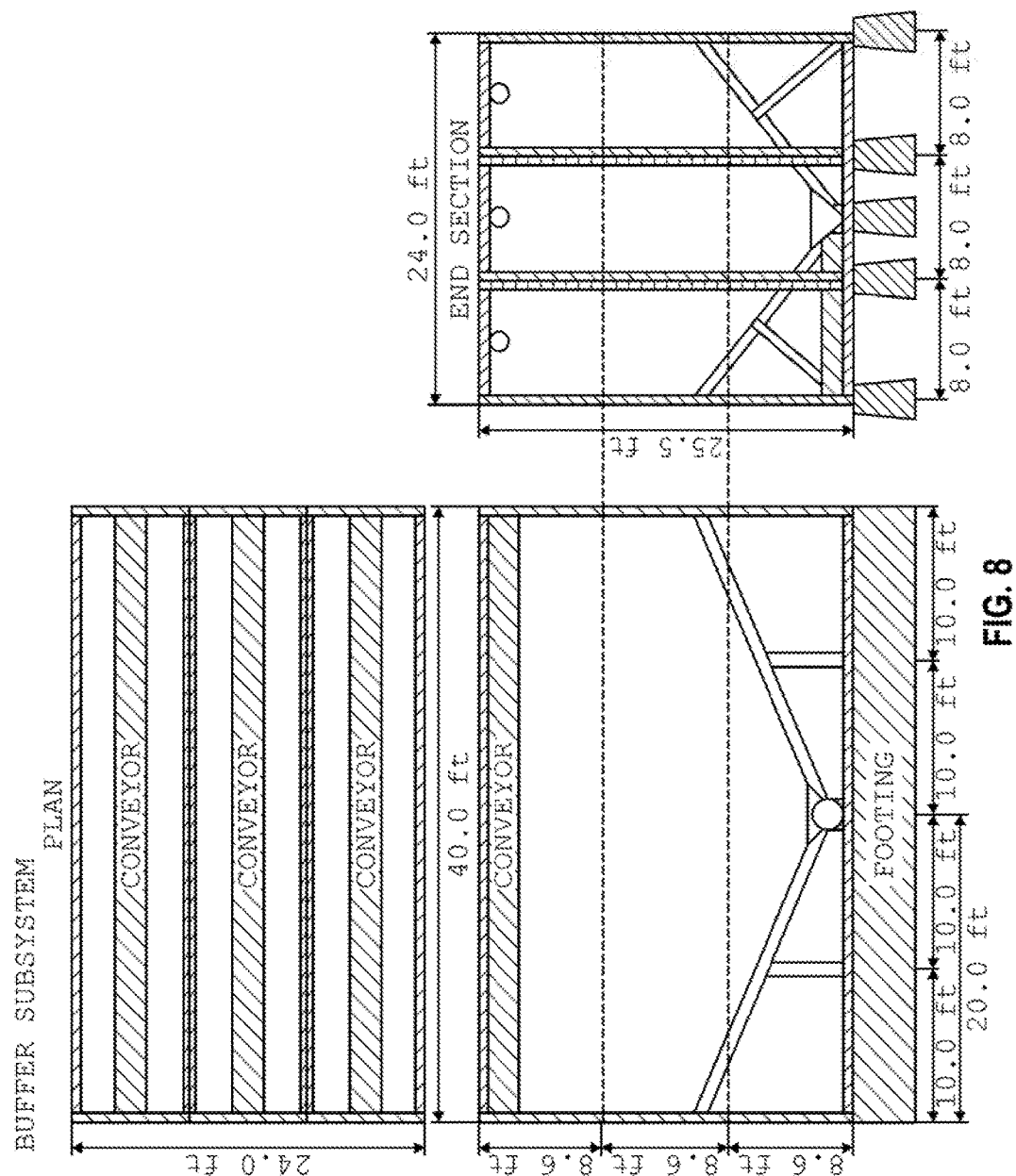
FIG. 8 depicts a plan view and two cross sections of a buffer tank, with input and output feeds, made up of nine prefabricated modules.

FIGS. 7 and 8 shows the flexibility of the type of design for building other types of vessels. FIG. 7 shows one section of a horizontal tank made up of three prefabricated modules while FIG. 8 shows a solid storage buffer with integrated feeders and distribution made up of nine modules. Wide array of other modules containing pumps, blower, heat exchangers controls, gasifiers and gas cleanup are not shown. The concept of instant invention is to develop a modularized biocolumn system which can be easily and conveniently assembled. The only site work while assembling the biocolumn includes grading, roads, fences, utilities and compacting of soil beneath the tanks. The entire system is prefabricated and factory tested for final assembly and commissioning on site.

Figure 9:
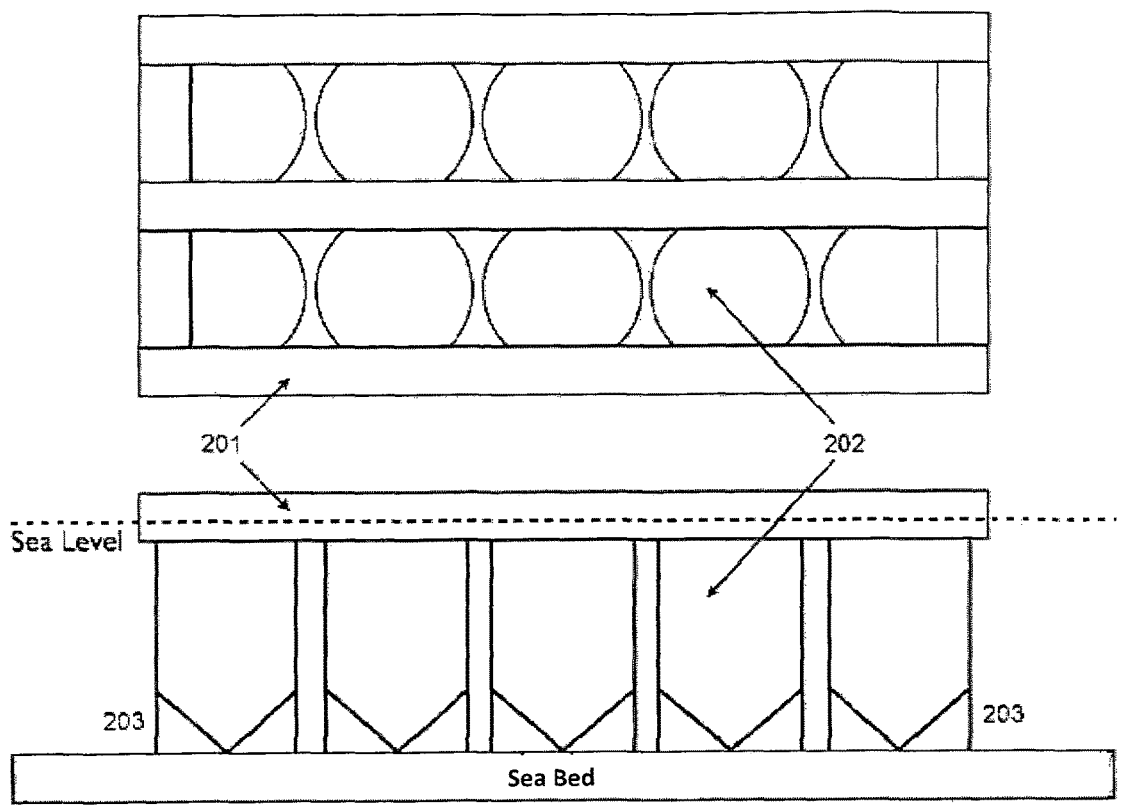
FIG. 9 depicts a plan view and cross sections of an array of ten biocolumn tanks supported by a floating structure tethered to the bottom of a body of water.
Figure 10:
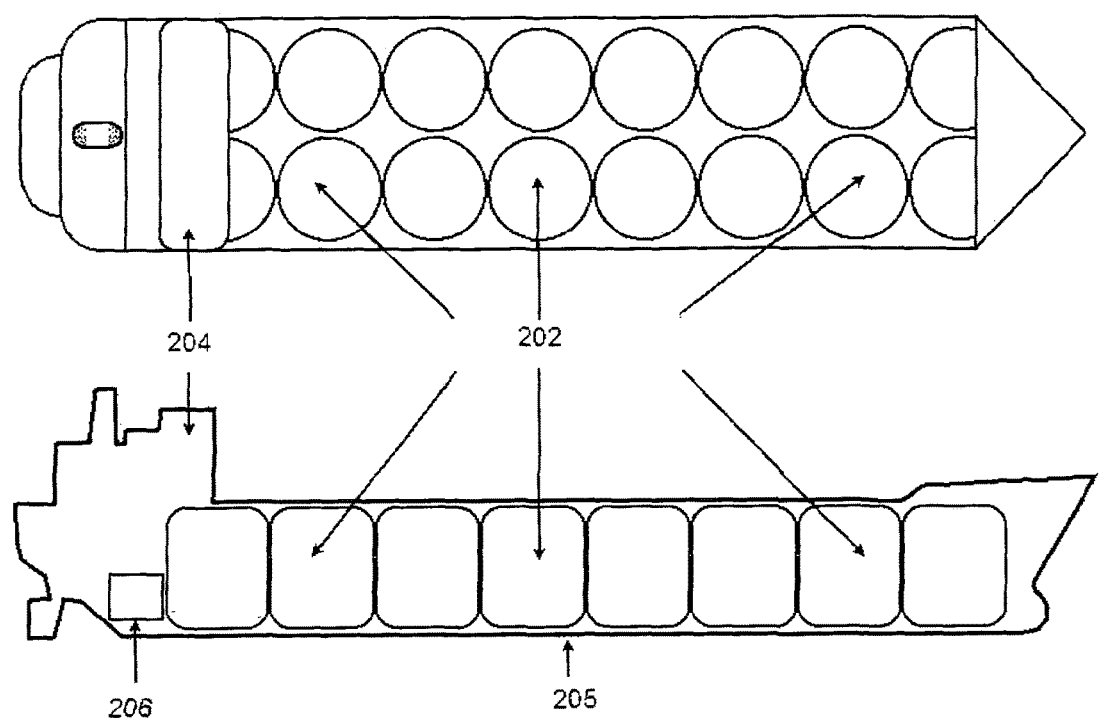
FIG. 10 depicts a plan view and cross sections of an array of sixteen biocolumn tanks fabricated inside the hull of a single, or double hulled tanker.

FIGS. 9 and 10 show methods of very large scale up with extremely low capital cost. Flexible tank walls are supported in a larger body of water to provide support with cables and anchors providing the shape need for the tanks. In FIG. 9 shows a waterborne array of biocolumn tanks (202) that can be submerged beneath the surface of an inlet, river, pond estuary, bay or any other natural or man-made body of water. Lightweight dome shaped platforms (201) moored just beneath the surface will use the weight of the water above to resist the upward pressure of any gas evolved. Flexible membranes will deploy along prepositioned cable structures as liquid is added. Tethers (203) are attached to the sea bed for keeping the entire structure stationary. In FIG. 10, the external water pressure is provided inside the hull (205) of a surplus oil tanker or other custom built floating structure. The structure comprises a bridge (204) for connecting and an engine room (206) is space for accommodating engine. These fabrication techniques offer opportunities for substantial reduction in capital cost and the elimination of the need for scarce and/or valuable land. As in the land based embodiment, all product removal can be external to the tanks.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for generating fuel stocks comprising a plurality of assembled zones, fabricated by stacking or laterally arranging, prefabricated modules,
   wherein said prefabricated modules form a biocolumn, said biocolumn comprised of an aerobic zone, a microaerophilic zone, an oxidizing zone, a redox microtransition zone, and a reducing zone;
   wherein each zone is connected with the preceding and subsequent zones to allow communication, exchange of nutrients, and symbiotic consumption between species from different zones; and
   wherein one or more of a nutrient, a renewable energy source, photon energy or a carbon source can be added into a zone and one or more of a fuel stock or by-product can be removed,
   wherein one or more by-products from each zone can be recycled back into any of the zones, wherein a biomass by-product of the aerobic zone is recycled into the microaerophilic zone and a biomass by-product of the microaerophilic zone is recycled into the redox microtransition zone or reducing zone,
   wherein photon energy is obtained from submerged LEDs and wherein said submerged LEDs are mounted on distributing tubes that provide nutrient input in such a manner as to sweep lenses of the submersed LEDs and prevent growth build up that would block light, wherein said nutrient is selected from a group consisting of a geothermal fluid, an organic waste slurry biomass, a coal, a hydrocarbon and combinations thereof.

2. The system for generating fuel stocks according to claim 1, wherein said renewable energy source is a geothermal energy, a solar thermal energy, a photovoltaic energy, an external waste heat, a heat of internal reactions or combinations thereof.

3. The system for generating fuel stocks according to claim 1 wherein said nutrient is water containing.

4. The system for generating fuel stocks according to claim 1, wherein said carbon source is selected from a group consisting of atmospheric air, a carbon dioxide source, an organic waste, a coal, a hydrocarbons, a geothermal fluid, an internal product of said consortium growth, propagation and reaction, and combinations thereof.

5. The system for generating fuel stocks according to claim 1, wherein said modules are interconnected to function as a complete biocolumn.

6. The system for generating fuel stocks according to claim 1, wherein LEDs operating at one-sixth of the normal intensity of sunlight at just a level at which algae growth plateaus, before additional light intensity is wasted or actually inhibits additional growth, are used.

7. The system for generating fuel stocks according to claim 1, wherein said LEDs are pulsed to allow proximate algae to recover from the acceptance of a photon and be ready to receive another are used.

* * * * *